(12) United States Patent
Hirokawa et al.

(10) Patent No.: US 10,018,597 B2
(45) Date of Patent: Jul. 10, 2018

(54) DETECTION SYSTEM AND DETECTION METHOD

(71) Applicant: KABUSHIKI KAISHA TOSHIBA, Tokyo (JP)

(72) Inventors: Junko Hirokawa, Tokyo (JP); Kazuo Watabe, Kanagawa (JP); Takahiro Omori, Kanagawa (JP); Takashi Usui, Saitama (JP); Osamu Nishimura, Kanagawa (JP); Akihiro Kasahara, Chiba (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 106 days.

(21) Appl. No.: 15/075,621

(22) Filed: Mar. 21, 2016

(65) Prior Publication Data

US 2016/0282311 A1    Sep. 29, 2016

(30) Foreign Application Priority Data

Mar. 24, 2015 (JP) ................. 2015-060889

(51) Int. Cl.
*G01N 29/07* (2006.01)
*G01N 29/36* (2006.01)
*G01N 29/14* (2006.01)

(52) U.S. Cl.
CPC ............. *G01N 29/14* (2013.01); *G01N 29/07* (2013.01); *G01N 29/36* (2013.01); *G01N 2291/0234* (2013.01); *G01N 2291/2698* (2013.01)

(58) Field of Classification Search
CPC . G01N 29/14; G01N 29/36; G01N 2291/0234
(Continued)

(56) References Cited

U.S. PATENT DOCUMENTS 2,867,788 A * 1/1959 Harry ................. G01S 1/72
367/113
5,681,995 A * 10/1997 Ooura .................. G01N 29/11
376/249
(Continued)

FOREIGN PATENT DOCUMENTS

CN     103852522 A  *  8/2014
JP     355060850     *  5/1980
(Continued)

OTHER PUBLICATIONS

Toda, et al., "Detection of wire-breaks during tensile testing", Proceedings of the Iron and Steel Institute of Japan annual meeting, 1 page (1979).

*Primary Examiner* — J M Saint Surin
(74) *Attorney, Agent, or Firm* — Finnegan, Henderson, Farabow, Garrett & Dunner, L.L.P.

(57) ABSTRACT

According to an embodiment, a detection system detects deterioration of a rope through at least one sheave. The system includes a plurality of sensors and a calculator. The sensors are configured to detect an elastic wave generated from the rope and convert the elastic wave into a detection signal. At least one of the sensors is installed near an end portion of the rope. At least one of the sensors is installed at the sheave. The calculator is configured to calculate a position of the rope where the elastic wave has been generated, based on a propagating speed of the elastic wave, time difference information of a plurality of detected times of the elastic waves detected by the respective sensors, and positional information indicating positions of the respective sensors.

7 Claims, 15 Drawing Sheets

(58) Field of Classification Search
USPC .......................................................... 73/587
See application file for complete search history.

(56) References Cited

U.S. PATENT DOCUMENTS

| | | | |
|---|---|---|---|
| 6,082,193 | A | 7/2000 | Paulson |
| 6,305,222 | B1 * | 10/2001 | Johnson ............. G01C 19/5684 |
| | | | 73/504.12 |
| 2006/0095223 | A1 * | 5/2006 | Gordon .................. G01N 29/07 |
| | | | 702/116 |
| 2011/0315489 | A1 | 12/2011 | Nakamori |

FOREIGN PATENT DOCUMENTS

| | | | |
|---|---|---|---|
| JP | 9-136776 | | 5/1997 |
| JP | 9-210859 | | 8/1997 |
| JP | 9-210860 | | 8/1997 |
| JP | 10-167650 | | 6/1998 |
| JP | 2001-508536 | | 6/2001 |
| JP | 2005-162379 | | 6/2005 |
| JP | 2007204263 | A * | 8/2007 |
| JP | 2010-89891 | | 4/2010 |
| JP | 2012-517391 | | 8/2012 |
| JP | 2012-520472 | | 9/2012 |
| JP | 2012-251391 | | 12/2012 |
| WO | WO 2010/105268 | | 9/2010 |

\* cited by examiner

| MAIN ROPE | TOTAL NUMBER OF RUPTURES | MAXIMUM NUMBER OF RUPTURES PER ONE PITCH | MAXIMUM NUMBER OF RUPTURES PER ONE STRAND PITCH |
|---|---|---|---|
| 5a | 30 | 16 | 2 |
| 5b | 50 | 10 | 3 |
| 5c | 60 | 12 | 1 |
| 5d | 40 | 8 | 2 |

US 10,018,597 B2

DETECTION SYSTEM AND DETECTION METHOD

CROSS-REFERENCE TO RELATED APPLICATION

This application is based upon and claims the benefit of priority from Japanese Patent Application No. 2015-060889, filed on Mar. 24, 2015; the entire contents of which are incorporated herein by reference.

FIELD

Embodiments described herein relate generally to a detection system and a detection method.

BACKGROUND

Technologies to examine deterioration of ropes used in elevators, cranes, and bridges are known. For example, a car and a counter weight of an elevator are hung in a hoistway with a plurality of main ropes. Wire ropes, resin-coated ropes, or the like are used for the main ropes. The wire rope includes a plurality of strands that is a plurality of twisted wires made of carbon steel or stainless steel. The wire rope is configured by twisting the plurality of strands around a rope core at predetermined pitches. Meanwhile, the resin-coated rope is a rope provided with resin-made coating on an outer periphery of a steel-made rope.

The main ropes are wound around a sheave of the elevator car, a sheave of the counter weight, and a sheave of the hoist. Deterioration such as abrasion and disconnection is caused in the strands and wires of the main ropes due to complex causes such as high frequent bending, tensile stress, and friction through the operation of the elevator. Therefore, examinations to confirm soundness of the main ropes are periodically performed in the operation of the elevator. As methods of examining the main ropes, for example, a method of taking the main ropes off the elevator device and performing an examination using a magnetic flow detector, and a method of visually examining the entire length of the main ropes by a maintenance worker while keeping the main ropes hung from the elevator device are known.

However, it has been difficult to examine the state of the ropes without depending on types of the ropes, in a state where the ropes are being used.

DETAILED DESCRIPTION

According to an embodiment, a detection system detects deterioration of a rope through at least one sheave. The system includes a plurality of sensors and a calculator. The sensors are configured to detect an elastic wave generated from the rope and convert the elastic wave into a detection signal. At least one of the sensors is installed near an end portion of the rope. At least one of the sensors is installed at the sheave. The calculator is configured to calculate a position of the rope where the elastic wave has been generated, based on a propagating speed of the elastic wave, time difference information of a plurality of detected times of the elastic waves detected by the respective sensors, and positional information indicating positions of the respective sensors.

Hereinafter, embodiments of a detection system and a detection method will be described in detail with reference to the appended drawings.

Figure 1:
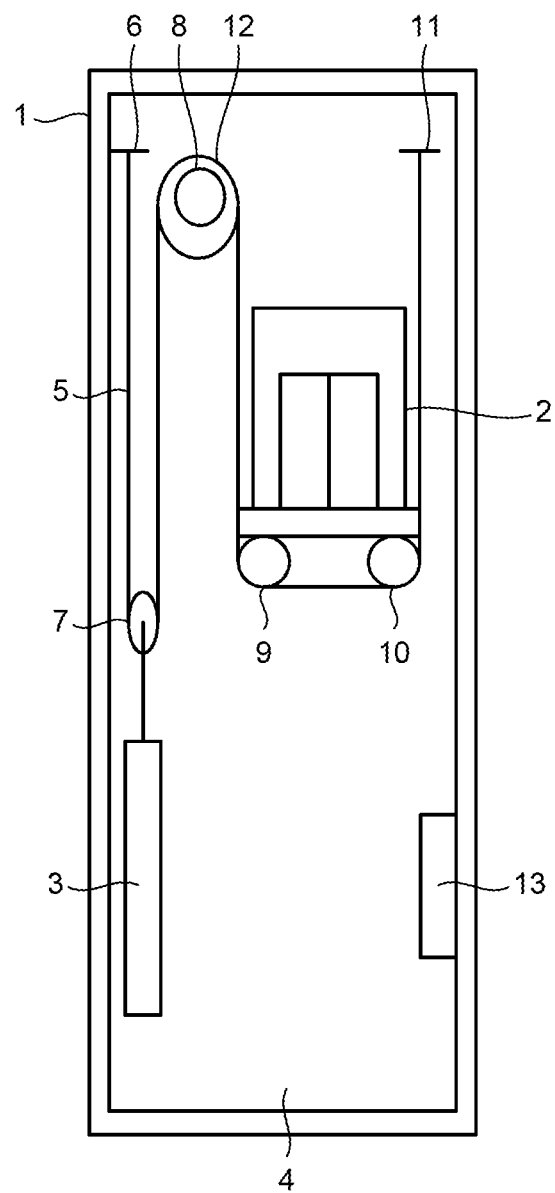
FIG. 1 is a schematic diagram illustrating an example of a structure of an elevator.

FIG. 1 is a schematic diagram illustrating an example of a structure of an elevator 1. A car 2 and a counter weight 3 move up and down in a hoistway 4 along a guide rail that is not illustrated in FIG. 1. Main ropes 5 hang the car 2 and the counter weight 3. The number of the main ropes 5 is four. Note that the number of the main ropes 5 is not limited to four. Types of the main ropes 5 include a wire rope, a resin-coated rope, and the like. The main ropes 5 have one ends fixed at an end portion 6, and the other ends fixed at the other end portion 11 through sheaves 7, 8, 9, and 10. The sheave 8 is connected to a hoist 12. The hoist 12 rotates the sheave 8, so that the car 2 and the counter weight 3 move up and down in the hoistway 4. Further, the elevator 1 includes a control panel 13 in the hoistway 4. The control panel 13 controls functions of the elevator 1. The control panel 13 is operated by a maintenance worker or the like of the elevator 1. The maintenance worker operates the control panel 13, thereby, for example, to adjust setting of speeds and accelerations of when the car 2 and the counter weight 3 move up and down, and the like.

Figure 2:
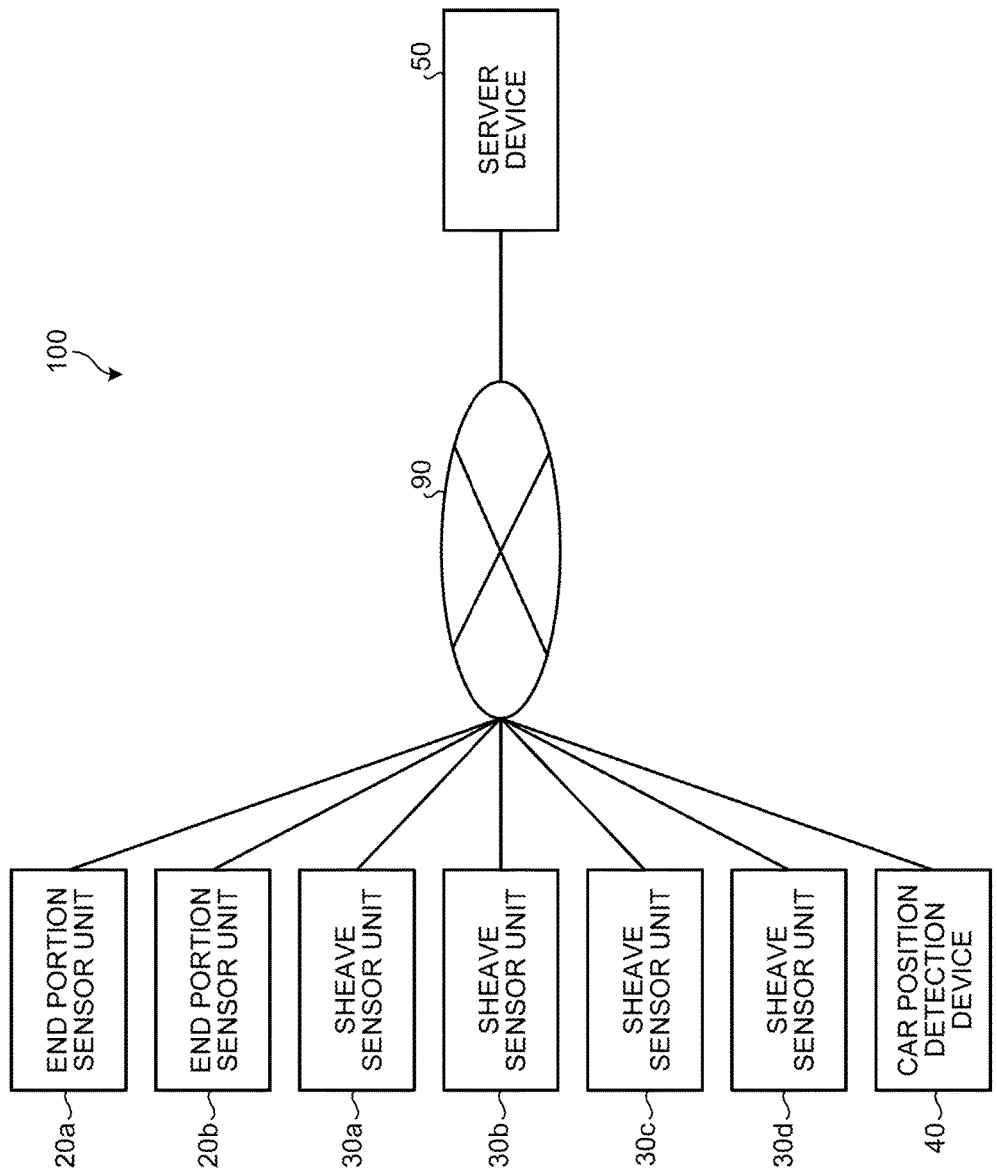
FIG. 2 is a diagram illustrating an example of a device configuration of a detection system of an embodiment.

FIG. 2 is a diagram illustrating an example of a device configuration of a detection system 100 of an embodiment. The detection system 100 of an embodiment includes an end portion sensor unit 20a, an end portion sensor unit 20b, a sheave sensor unit 30a, a sheave sensor unit 30b, a sheave sensor unit 30c, a sheave sensor unit 30d, a car position detection device 40, and a server device 50. The end portion sensor unit 20a, the end portion sensor unit 20b, the sheave sensor unit 30a, the sheave sensor unit 30b, the sheave sensor unit 30c, the sheave sensor unit 30d, the car position detection device 40, and the server device 50 are connected through a network 90. A communication system of the network 90 is a wireless communication system, for example.

The end portion sensor unit 20a is installed at or near the end portion 6 of the main ropes 5. The end portion sensor unit 20b is installed at or near the end portion 11 of the main ropes 5.

The sheave sensor unit 30a is installed at the sheave 7. The sheave sensor unit 30b is installed at the sheave 8. The sheave sensor unit 30c is installed at the sheave 9. The sheave sensor unit 30d is installed at the sheave 10.

Hereinafter, when the end portion sensor unit 20a and the end portion sensor unit 20b are not distinguished, they are simply called end portion sensor unit 20. Similarly, when the sheave sensor unit 30a, the sheave sensor unit 30b, the sheave sensor unit 30c, and the sheave sensor unit 30d are not distinguished, they are simply called sheave sensor unit 30.

The car position detection device 40 (corresponds to a detector) detects the position of the car 2. The car position detection device 40 transmits, to a server device 50, car position information in which time information and information indicating the position of the car 2 at a time indicated by the time information are associated with each other.

The server device 50 receives detected time information and feature amount information described below from the end portion sensor unit 20 as end portion sensor unit information. Further, the server device 50 receives detected time information, feature amount information, and rotation angle information described below from the sheave sensor unit 30 as sheave sensor unit detection information. Further, the server device 50 receives car positional information from the car position detection device 40. The server device 50 performs processing of calculating the position of the main rope 5 where an elastic wave has been generated, and processing of diagnosing deterioration of the main rope 5.

Next, an example of a configuration of the end portion sensor unit 20 of an embodiment will be described.

Figure 3:
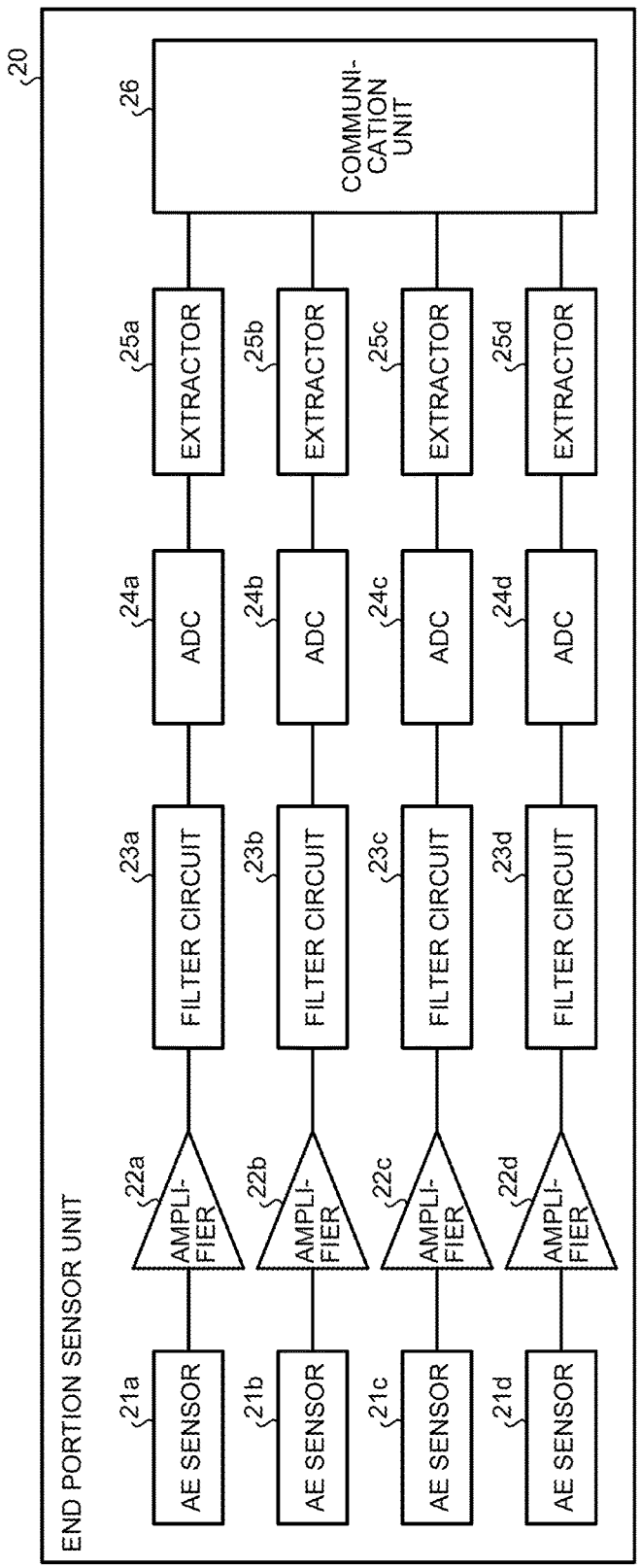
FIG. 3 is a diagram illustrating an example of a configuration of an end portion sensor unit of an embodiment.

FIG. 3 is a diagram illustrating an example of a configuration of the end portion sensor unit 20 of an embodiment. The end portion sensor unit 20 of an embodiment includes acoustic emission (AE) sensors 21a to 21d, amplifiers 22a to 22d, filter circuits 23a to 23d, AD converters (ADCs) 24a to 24d, extractors 25a to 25d, and a communication unit 26. The AE sensors 21a to 21d are installed at or near the respective end portions 6 (11) of the four main ropes 5.

Hereinafter, when the AE sensors 21a to 21d are not distinguished, they are simply called AE sensor 21. Similarly, when the amplifiers 22a to 22d are not distinguished, they are simply called amplifier 22. Further, when the filter circuits 23a to 23d are not distinguished, they are simply called filter circuit 23. Further, when the ADCs 24a to 24d are not distinguished, they are simply called ADC 24. Further, when the extractors 25a to 25d are not distinguished, they are simply called extractor 25.

The AE sensor 21 detects the elastic wave generated from the main rope 5, and converts the elastic wave into a detection signal such as a voltage signal or the like. The AE sensor 21 is a sensor using a piezoelectric element. The elastic wave is generated in association with development of the deterioration of the main rope 5, and is detected as an indication of wire cut of the main rope 5 before the main rope 5 reaches the wire cut. Therefore, the frequency of generation of the elastic wave and signal intensity of the elastic wave are useful as indexes that indicate soundness of the main rope 5. The AE sensor 21 inputs the detection signal to the amplifier 22.

The amplifier 22 amplifies the detection signal when having received the detection signal from the AE sensor 21. The amplifier 22 inputs the amplified detection signal to the filter circuit 23.

When having received the amplified detection signal from the amplifier 22, the filter circuit 23 removes, from the amplified detection signal, signal components other than a signal band that indicates the elastic wave. The filter circuit 23 inputs, to the ADC 24, the detection signal from which the signal components other than the signal band that indicates the elastic wave have been removed.

When having received the detection signal from which the signal components other than the signal band that indicates the elastic wave have been removed, from the AE sensor 21, the ADC 24 quantizes the detection signal, thereby to convert a data format of the detection signal from an analog format to a digital format. The ADC 24 inputs the detection signal in a data format, which has been converted into the digital data format, to the extractor 25.

When having received the detection signal from the ADC 24, the extractor 25 determines whether the detection signal is a threshold (first threshold) or more. When the detection signal is the threshold or more, the extractor 25 stores the detected time information that indicates a time when having received the detection signal. Then, the extractor 25 extracts the feature amount information that indicates a feature of the detection signal from the detection signal.

The feature amount information is, for example, an amplitude of a waveform of the detection signal [mV], a duration of the waveform of the detection signal [μsec], the number of zero cross counts of the detection signal [times], energy of the waveform of the detection signal [arb.], and a frequency of the detection signal [Hz].

The extractor 25 inputs the detected time information and the feature amount information to the communication unit 26. When having received the detected time information and the feature amount information from the extractor 25, the communication unit 26 transmits the detected time information and the feature amount information to the server device 50 as end portion sensor unit detection information together with identification information that identifies the AE sensor 21 that detects the elastic wave.

Next, an example of a configuration of the sheave sensor unit 30 of an embodiment will be described.

Figure 4:
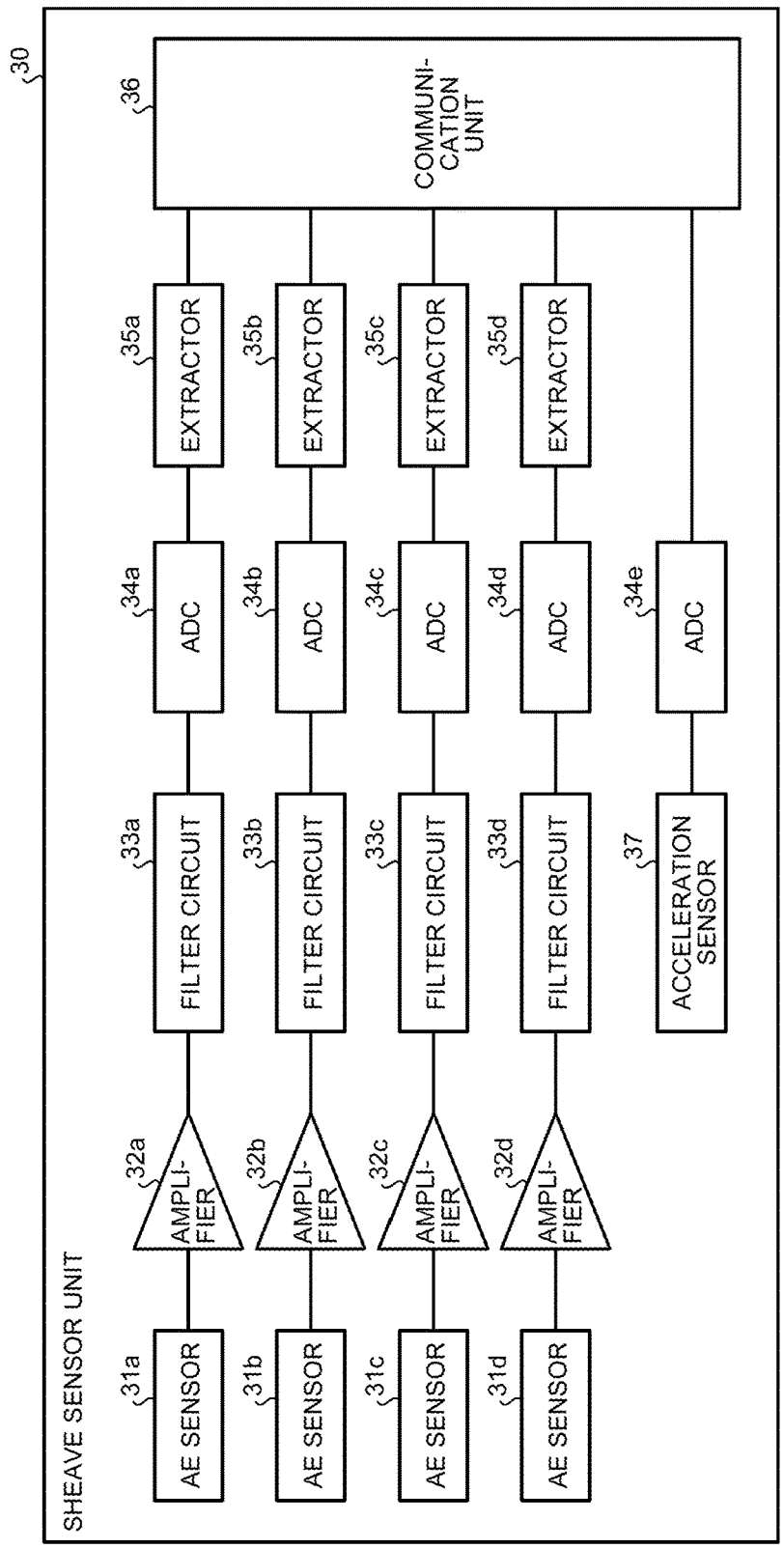
FIG. 4 is a diagram illustrating an example of a configuration of a sheave sensor unit of an embodiment.

FIG. 4 is a diagram illustrating an example of a configuration of the sheave sensor unit 30 of an embodiment. The sheave sensor unit 30 of an embodiment includes AE sensors 31a to 31d, amplifiers 32a to 32d, filter circuits 33a to 33d, ADCs 34a to 34e, extractors 35a to 35d, a communication unit 36, and an acceleration sensor 37.

Hereinafter, when the AE sensors 31a to 31d are not distinguished, they are simply called AE sensor 31. Similarly, when the amplifiers 32a to 32d are not distinguished, they are simply called amplifier 32. Further, when the filter circuits 33a to 33d are not distinguished, they are simply called filter circuit 33. Further, when the ADCs 34a to 34e are not distinguished, they are simply called ADC 34. When the extractors 35a to 35d are not distinguished, they are simply called extractor 35.

Here, installation positions of the AE sensors 31a to 31d and the acceleration sensor 37 will be described using a case of the sheave sensor unit 30b installed in the sheave 8 as an example. First, installation positions of the AE sensor 31a, the AE sensor 31b, and the acceleration sensor 37 will be described.

Figure 5:
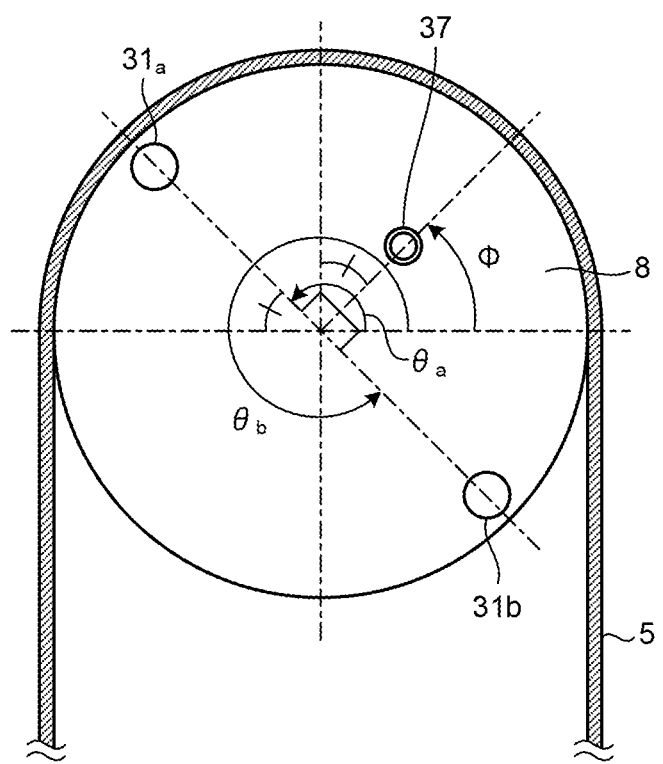
FIG. 5 is a schematic diagram illustrating an example of a front surface of a sheave of a hoist.

FIG. 5 is a schematic diagram illustrating an example of a front surface of the sheave 8 of the hoist 12. As illustrated in FIG. 5, the AE sensor 31a and the AE sensor 31b are installed in the sheave 8 at a phase difference π of a rotation angle of the sheave 8. Accordingly, even if the sheave 8 is rotated, at least one of the AE sensors 31a and 31b can be always in a position near the main ropes 5. The example of FIG. 5 illustrates that the AE sensor 31a is in the position near the main ropes 5.

The acceleration sensor 37 is installed in a position different from the AE sensor 31a and the AE sensor 31b by a π/2 phase. With the acceleration sensor 37, a rotation angle φ that indicates the position of the acceleration sensor 37 is known. Accordingly, from the positional relationship between the acceleration sensor 37 and the AE sensor 31a, a rotation angle $\theta_a$ (=φ+π/2) that indicates the position of the AE sensor 31a is known. Similarly, from the positional relationship between the acceleration sensor 37 and the AE sensor 31b, a rotation angle $\theta_b$ (=φ+3π/2) that indicates the position of the AE sensor 31b is known.

Next, installation positions of the AE sensor 31c and the AE sensor 31d will be described.

Figure 6:
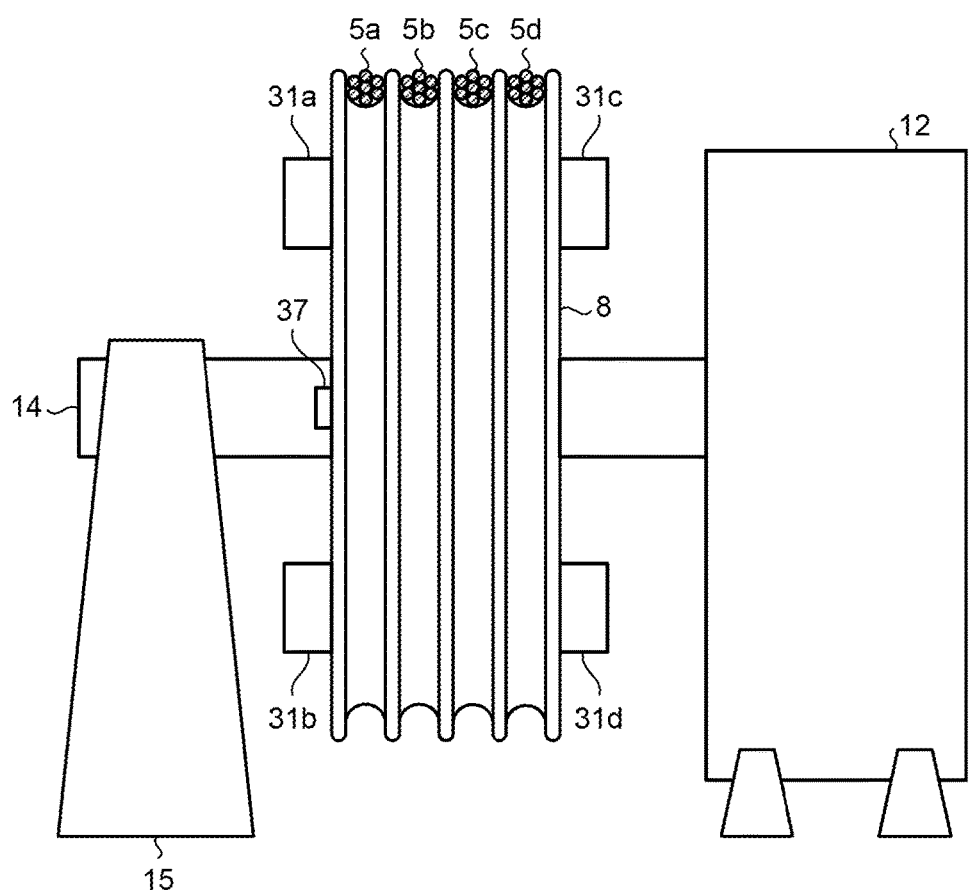
FIG. 6 is a schematic diagram illustrating an example of a side surface of a sheave of a hoist.

FIG. 6 is a schematic diagram illustrating an example of a side surface of the sheave 8 of the hoist 12. A rotating shaft 14 of the hoist 12 is rotated, so that the sheave 8 is rotated. A bearing 15 supports the rotating shaft 14. The AE sensor 31c is installed at the same position on an opposite surface of the sheave 8 where the AE sensor 31a is installed, for example. Further, the AE sensor 31d is installed at the same position on an opposite surface of the sheave 8 where the AE sensor 31b is installed, for example. Accordingly, the elastic waves of the main ropes 5a to 5d can be detected from both sides of the sheave 8. Therefore, from which main rope 5 of the main ropes 5a to 5d the elastic wave has been generated can be calculated. Note that the rotation angles detected on the both sides are the same, and thus the acceleration sensor 37 may just be installed on at least one surface of the sheave 8.

Referring back to FIG. 4, each of the AE sensors 31a to 31d detects the elastic wave and noises generated from the main ropes 5, and converts the elastic wave and the noises into the detection signal such as the voltage signal. The AE sensor 31a (31b, 31c, or 31d) inputs the detection signal to the amplifier 32a (32b, 32c, or 32d).

When having received the detection signal from the AE sensor 31a (31b, 31c, or 31d), the amplifier 32a (32b, 32c, or 32d) amplifies the detection signal. The amplifier 32a (32b, 32c, or 32d) inputs the amplified detection signal to the filter circuit 33a (33b, 33c, or 33d).

When having received the amplified detection signal from the amplifier 32a (32b, 32c, or 32d), the filter circuit 33a (33b, 33c, or 33d) removes, from the amplified detection signal, the signal components other than the signal band that indicates the elastic wave. The filter circuit 33a (33b, 33c, or 33d) inputs, to the ADC 34a (34b, 34c, or 34d), the detection signal from which the signal components other than the signal band that indicates the elastic wave have been removed.

Note that detection processing of the respective AE sensors 31a to 31d and processing of acquiring the rotation angle information by the acceleration sensor 37 described below are synchronized with each other, and the detection processing of the respective AE sensors 31a to 31d and the processing of acquiring the rotation angle information by the acceleration sensor 37 are performed at the same timing.

When having received the detection signal from the AE sensor 31a (31b, 31c, or 31d), the ADC 34a (34b, 34c, or 34d) quantizes the detection signal, thereby to convert the data format of the detection signal from an analog format to a digital format. The ADC 34a (34b, 34c, or 34d) inputs the detection signal in a data format, which has been converted into the digital data format, to the extractor 35a (35b, 35c, or 35d).

When having received the detection signal from the ADC 34a (34b, 34c, or 34d), the extractor 35a (35b, 35c, or 35d) stores the detected time information that indicates a time when having received the detection signal. Note that the timings of the detection processing of the respective AE sensors 31a to 31d are synchronized with each other. Therefore, any one extractor 35 of the extractors 35a (35b, 35c, and 35d) may store the detected time information.

Further, the extractor 35a (35b, 35c, or 35d) extracts the feature amount information that indicates a feature of the detection signal from the detection signal. Further, the extractor 35 inputs the detected time information and the feature amount information to the communication unit 36.

The communication unit 36 receives the detected time information and the feature amount information from the extractors 35a to 35d. Further, the communication unit 36 receives the rotation angle information described below from the ADC 34e. The communication unit 36 transmits, to the server device 50, the detected time information and the feature amount information received from the extractors 35a to 33d and the rotation angle information in association with each other as the sheave sensor unit detection information. Note that the detected time information and the feature amount information are transmitted together with the identification information that indicates the AE sensor 31 that has detected the elastic wave corresponding to the detected time information and the feature amount information.

The acceleration sensor 37 detects the rotation angle φ (see FIG. 5) that indicates the position of the acceleration sensor 37. The acceleration sensor 37 inputs the rotation angle information that indicates the rotation angle φ to the ADC 34e.

When having received the rotation angle information from the acceleration sensor 37, the ADC 34e quantizes the rotation angle information, thereby to convert the data format of the rotation angle information from an analog format to a digital format. The ADC 34e inputs the rotation angle information in a data format, which has been converted into the digital data format, to the communication unit 36.

Next, an example of functional configurations of the server device 50 of an embodiment will be described.

Figure 7:
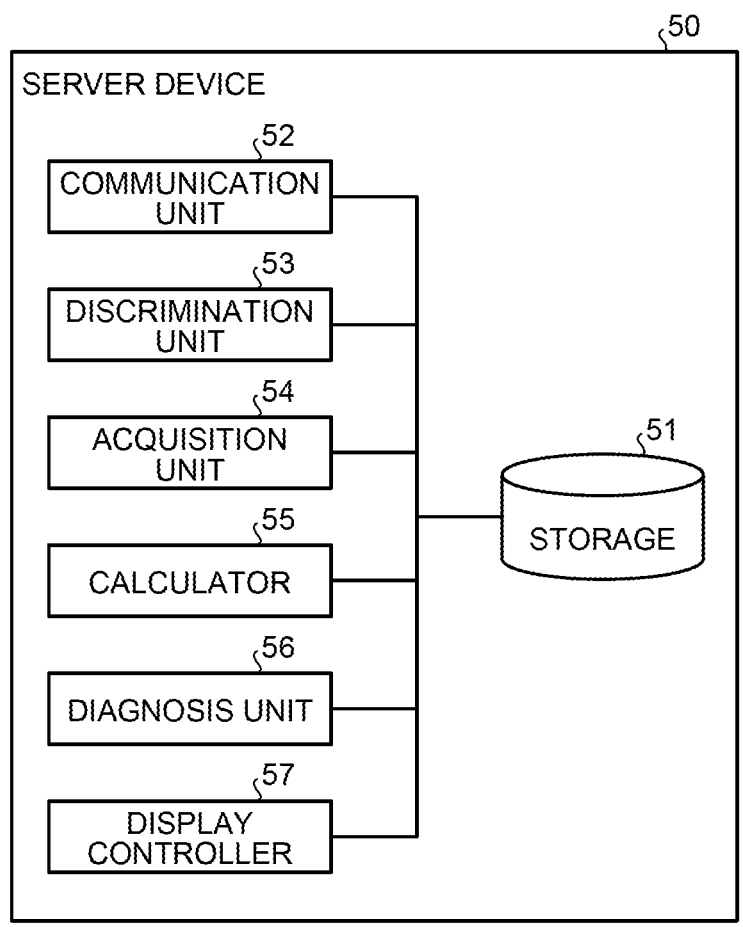
FIG. 7 is a diagram illustrating an example of a functional configuration of a server device of an embodiment.

FIG. 7 is a diagram illustrating an example of functional configurations of the server device 50 of an embodiment. The server device 50 of an embodiment includes a storage 51, a communication unit 52, a discrimination unit 53, an acquisition unit 54, a calculator 55, a diagnosis unit 56, and a display controller 57.

The storage 51 stores information. The information stored in the storage 51 includes the end portion sensor unit detection information (the detected time information and the feature amount information) received from the end portion sensor unit 20, the sheave sensor unit detection information (the detected time information, the feature amount information, and the rotation angle information) received from the sheave sensor unit 30, the car positional information received from the car position detection device 40, distance information, and the like. In the distance information, distances between the end portion 6, the sheaves 7, 8, 9, and 10, and the end portion 11 determined according to the position of the car 2 are stored.

Further, the storage 51 stores the feature amount information from which the noises have been removed by processing of the acquisition unit 54 described below in association with the sheave sensor unit detection information. Further, the storage 51 stores deterioration positional information obtained by processing of the calculator 55 described below.

When having received the end portion sensor unit detection information from the end portion sensor unit 20, the communication unit 52 stores the end portion sensor unit detection information in the storage 51. Further, when having received the sheave sensor unit detection information from the sheave sensor unit 30, the communication unit 52 stores the sheave sensor unit detection information in the storage 51. Further, when having received the car positional information from the car position detection device 40, the communication unit 52 stores the car positional information in the storage 51.

The discrimination unit 53 reads, from the storage 51, the sheave sensor unit detection information (the detected time information, the feature amount information, and the rotation angle information), and discriminates a feature amount that indicates the elastic wave (including the noises) and a feature amount that indicates the noises.

Discrimination processing of the discrimination unit 53 will be specifically described using a case of the sheave sensor unit detection information received from the sheave sensor unit 30b installed at the sheave 8 as an example.

First, the discrimination unit 53 calculates the rotation angle $\theta_a$ that indicates the positions of the AE sensor 31a and the AE sensor 31c, and the rotation angle $\theta_b$ that indicates the positions of the AE sensor 31b and the AE sensor 31d, from the rotation angle $\varphi$ (see FIG. 5) indicated by the rotation angle information. Next, the determination unit 53 discriminates the feature amount information that indicates the detection signal acquired by the AE sensor 31 at the rotation angle of from 0 to $\pi$, exclusive of $\pi$ (or from 0 to $\pi$, exclusive of 0), of the rotation angles $\theta_a$ and $\theta_b$, as the feature amount information that indicates the elastic wave. Further, the discrimination unit 53 discriminates the feature amount information that indicates the detection signal acquired by the AE sensor 31 at the rotation angle of from $\pi$ to $2\pi$, exclusive of $2\pi$ (or from $\pi$ to $2\pi$, exclusive of $\pi$), of the rotation angles $\theta_a$ and $\theta_b$, as the feature amount information that indicates the noises. The discrimination unit 53 inputs the feature amount information that indicates the elastic wave and the feature amount information that indicates the noises to the acquisition unit 54.

When having received the feature amount information that indicates the elastic wave and the feature amount information that indicates the noises from the discrimination unit 53, the acquisition unit 54 acquires the feature amount information that indicates the elastic wave, from which the noises are removed, by subtracting the feature amount information that indicates the noises from the feature amount information that indicates the elastic wave. To be specific, in the case of FIG. 5, the acquisition unit 54 acquires the feature amount information that indicates the elastic wave, from which the noises are removed, by subtracting the feature amount information that indicates the detection signal acquired by the AE sensor 31b from the feature amount information that indicates the detection signal acquired by the AE sensor 31a. The acquisition unit 54 performs the same processing for the feature amounts that indicate the detection signals acquired by the AE sensors 31c and 31d installed in the same positions on the opposite surface of the surface of the sheave 8 illustrated in FIG. 5. The acquisition unit 54 stores, in the storage 51, the feature amount information from which the noises have been removed in association with the sheave sensor unit detection information.

The calculator 55 reads, from the storage 51, the feature amount information of the end portion sensor unit detection information, and the feature amount information (from which the noises have been removed) of the sheave sensor unit detection information, and performs processing of calculating the position of the main ropes 5 where the elastic wave has been generated.

Next, details of the position calculation processing will be described. First, the calculator 55 divides a plurality of pieces of the feature amount information into groups based on whether the similarity of the feature amount information is a threshold (second threshold) or more. Then, the calculator 55 recognizes the feature amount information included in the same group as the feature amount information that indicates the elastic wave of the same generation source.

Note that the similarity is determined according to a distance between the feature amount information and the feature amount information. That is, the similarity is larger as the distance between different pieces of the feature amount information is closer. The calculator 55 calculates the distance between the feature amount information by a predetermined distance function. The distance function is a function for calculating a standard Euclidean distance, a Minkowski distance, or a Mahalanobis distance. Especially, the Mahalanobis distance enables calculation of the distance, considering correlation between the feature amount information, and can improve classification accuracy of the groups.

The calculator 55 calculates time difference information from the detected time information of the detection signal corresponding to the feature amount information having the similarity being the threshold or more (the feature amount information of the detection signal included in the same group). Then, the calculator 55 calculates two pieces of the detected time information in which the time difference information becomes smallest, and acquired by the AE sensor 21 and the AE sensor 31 included in different sensor units. Accordingly, the calculator 55 calculates the position of the generation source of the elastic wave from the detected time information of the elastic wave acquired by the closest two sensor units that sandwich the generation source of the elastic wave.

A method of calculating the position of the generation source of the elastic wave will be specifically described using a case of using the detected time information acquired by the sheave sensor unit 30a installed at the sheave 7, and the detected time information acquired by the sheave sensor unit 30b installed at the sheave 8, as an example.

Figure 8:
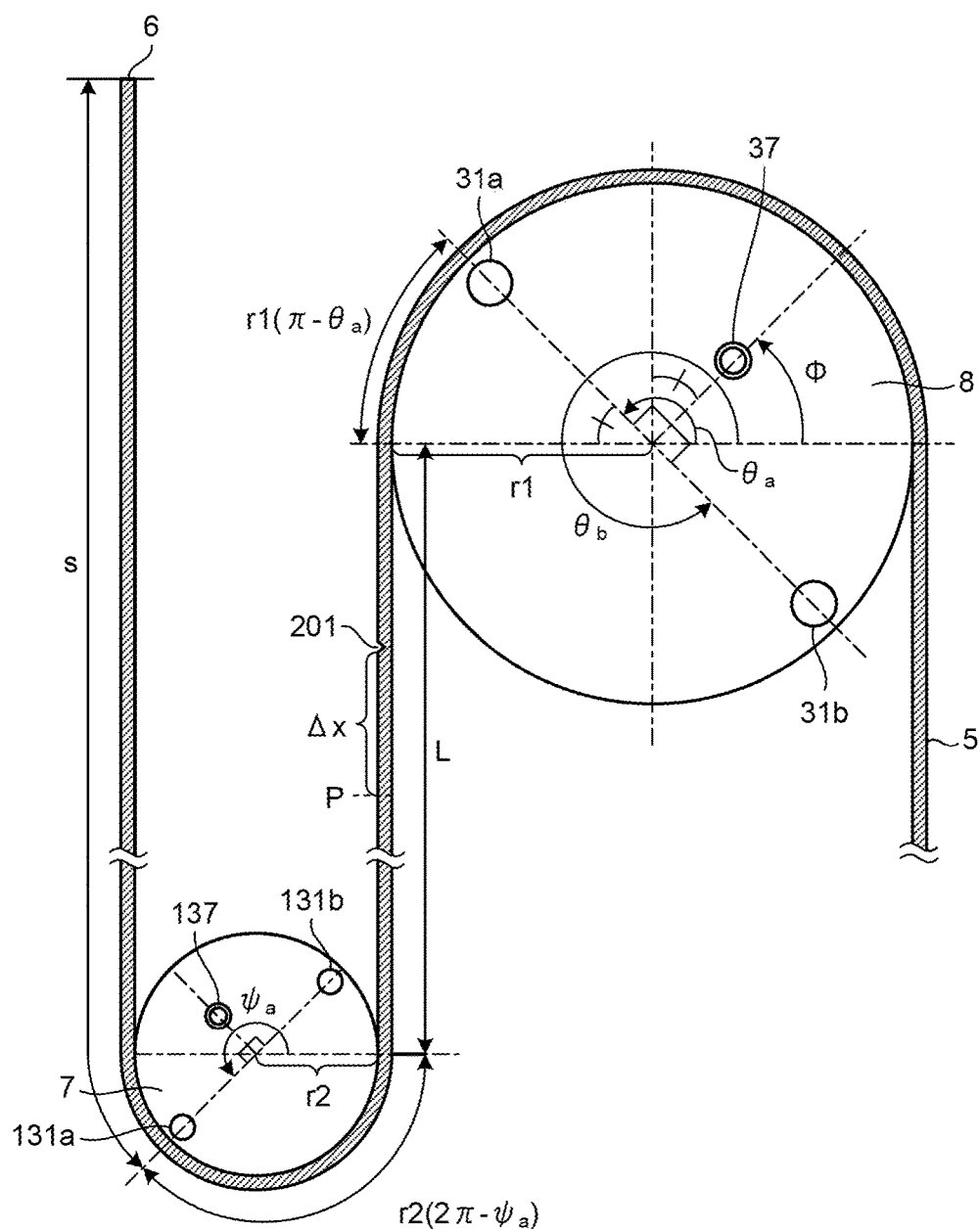
FIG. 8 is a diagram for describing an example of a method of calculating a position of a generation source of an elastic wave of an embodiment.

FIG. 8 is a diagram for describing an example of a method of calculating the position of a generation source 201 of the elastic wave of an embodiment. A time indicated by the detected time information acquired by the AE sensor 31a is T, and a time indicated by the detected time information acquired by an AE sensor 131a is T+$\Delta$t. That is, $\Delta$t indicates the time difference information calculated by the calculator 55.

The calculator 55 calculates the car position indicated by the car position information associated with the time information closest to the time T, by referring to the car positional information stored in the storage 51. The calculator 55 calculates a distance L between the sheave 7 and the sheave 8 determined according to the car position, by referring to the distance information stored in the storage 51.

A radius of the sheave 8 is r1, the rotation angle that indicates the position of the AE sensor 31a is $\theta_a$, a radius of the sheave 7 is r2, and the rotation angle that indicates the position of the AE sensor 131a is $\Psi_a$. The calculator 55 calculates a distance S from the AE sensor 31a to the AE sensor 131a by the following Equation (1):

$$S=r1(\pi-\theta_a)+L+r2(2\pi-\Psi_a) \quad (1)$$

When an intermediate point between the AE sensor 131a and the AE sensor 31a is P, the distance from the AE sensor 131a to P is S/2. At this time, the distance from the AE sensor 131a to the generation source 201 of the elastic wave is (S/2)+Δx. The calculator 55 calculates Δx using the relationship of the following Equation (2):

$$\Delta t=\{((S/2)+\Delta x)-((S/2)-\Delta x)\}/v=2\Delta x/v \quad (2)$$

Here, v is a propagating speed [m/s] of the elastic wave determined according to quality of material of the main rope 5.

Further, the calculator 55 calculates a distance s from the end portion 6 to the AE sensor 131a of the sheave 7 by a method similar to the above-described method. Accordingly, the calculator 55 can calculate a length l from the end portion 6 to the generation source 201 of the elastic wave by the following Equation (3):

$$l=s+(S/2)+\Delta x \quad (3)$$

Referring back to FIG. 7, next, the calculator 55 compares the feature amount information (from which the noises have been removed) associated with the detected time information acquired by the AE sensor 31a and the AE sensor 131a, and the feature amount information (from which the noises have been removed) associated with the detected time information acquired by the AE sensor 31c and the AE sensor 131c installed in the same positions on the opposite surface of the surface illustrated in FIG. 8. The calculator 55 calculates the main rope 5 where the elastic wave has been generated from the four main ropes 5, by comparing the magnitude of the energy of the waveforms of the elastic waves, as the feature amount information, for example. To be specific, the calculator 55 calculates the main rope 5a (5b, 5c, or 5d) where the elastic wave has been generated, by comparing a difference of the magnitude of the energy of the waveforms of the elastic waves acquired in the same position on both sides of the sheave 7 and the sheave 8 (for example, by the AE sensor 31a and the AE sensor 131a), and a range of a threshold (third threshold) that indicates that the elastic wave has been generated in the main rope 5a (5b, 5c, or 5d).

The calculator 55 stores, in the storage 51, deterioration positional information in which the positional information that indicates the generation source of the elastic wave and the feature amount information of the elastic wave are associated with each other. The positional information that indicates the generation source of the elastic wave includes identification information that identifies the main rope, and information that indicates the length from the end portion 6 or the end portion 11 to the generation source of the elastic wave, for example.

The diagnosis unit 56 reads the deterioration positional information from the storage 51, and diagnoses the degree of deterioration of the main rope 5. When there is a place where total energy of the elastic wave becomes predetermined energy or more, the diagnosis unit 56 performs display of a warning that indicates a risk of deterioration in the place, through the display controller 57.

The display controller 57 performs display control based on the deterioration positional information stored in the storage 51.

Figure 9:
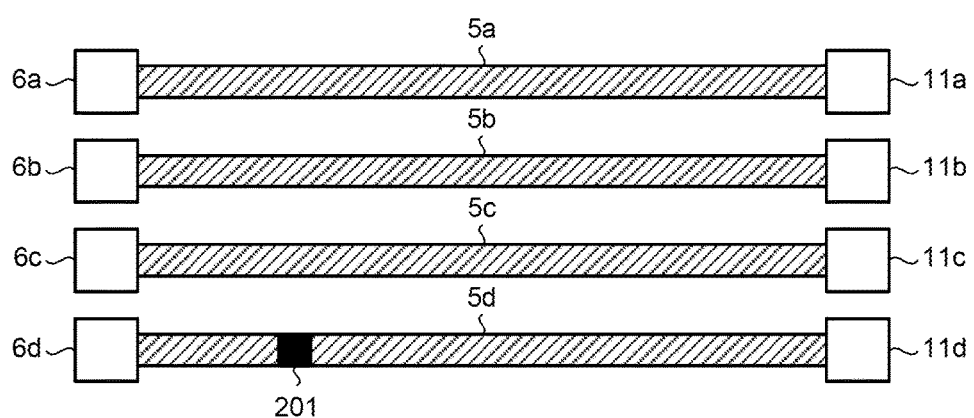
FIG. 9 is a diagram illustrating an example of display information indicating deterioration positional information of an embodiment.

FIG. 9 is a diagram illustrating an example of display information that indicates the deterioration positional information of an embodiment. The example of FIG. 9 indicates a case of linearly displaying the main ropes 5 (5a to 5d) fixed at the end portions 6 (6a to 6d) and the end portions 11 (11a to 11d). The display controller 57 performs display control of applying a color to the generation source (deterioration position) 201 of the elastic wave according to the degree of deterioration and displaying the generation source, for example.

Figure 10:
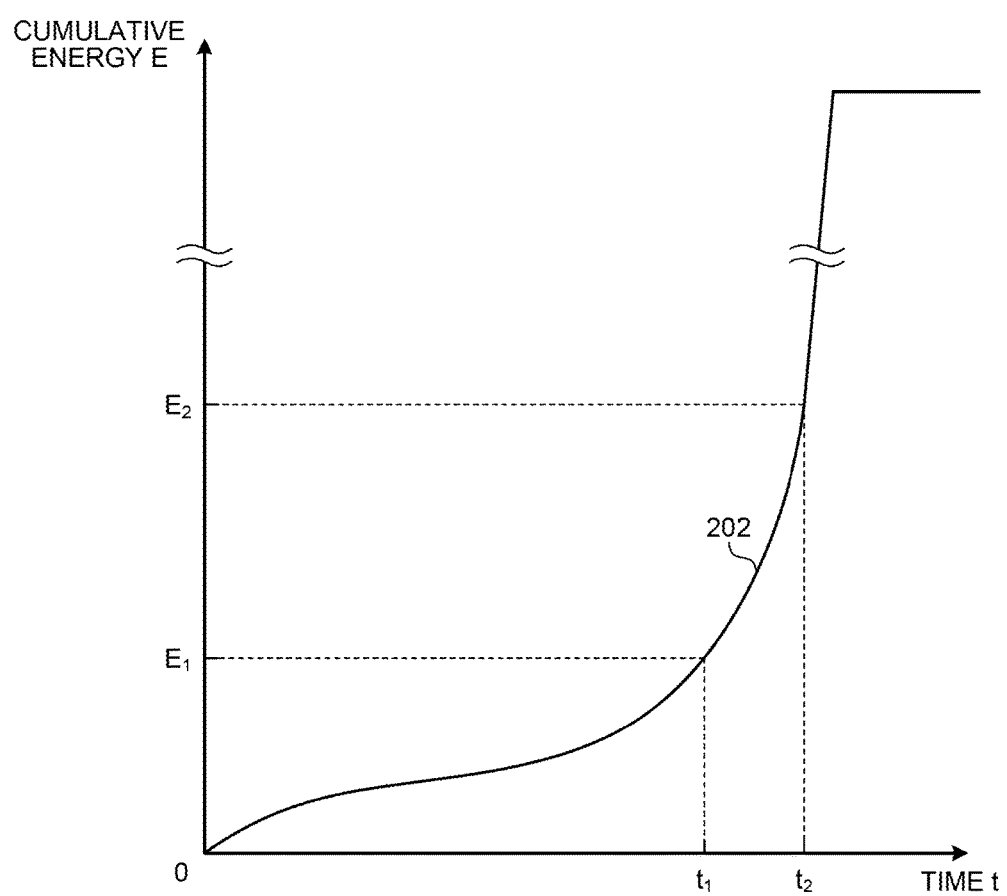
FIG. 10 is a diagram illustrating an example of display information indicating cumulative energy of an embodiment.

FIG. 10 is a diagram illustrating an example of the display information that indicates cumulative energy of an embodiment. FIG. 10 illustrates a case of displaying the cumulative energy by a curved line 202. The display controller 57 performs control of displaying the display information illustrated in FIG. 10 when there is an input that indicates selection of the generation source (deterioration position) 201 of the elastic wave while the display information illustrated in FIG. 9 is being displayed, for example.

In FIG. 10, $E_1$ is a threshold (fourth threshold) used when the state of the deterioration of the main rope 5d is diagnosed by the diagnosis unit 56. That is, the diagnosis unit 56 requests the display controller 57 to display a warning or the like that indicates that the degree of deterioration is large at a time $t_1$ when a value of the cumulative energy becomes $E_1$. Accordingly, an administrator of an elevator or the like can grasp a high possibility of causing a rupture of the main rope 5d before the rupture of the main rope 5d is caused due to further development of the deterioration. Note that the example of FIG. 10 indicates a case in which the rupture of the main rope 5d is caused at a time $t_2$. At and after the cumulative energy $E_2$, the cumulative energy E is sharply increased due to impact at the time of the rupture of the main rope 5d. Then, after the rupture, the cumulative energy E becomes constant. The diagnosis unit 56 diagnoses the deterioration position of the main rope 5 where the cumulative energy E after the rupture becomes constant as a place where wire cut has occurred.

Figures 11, 12:
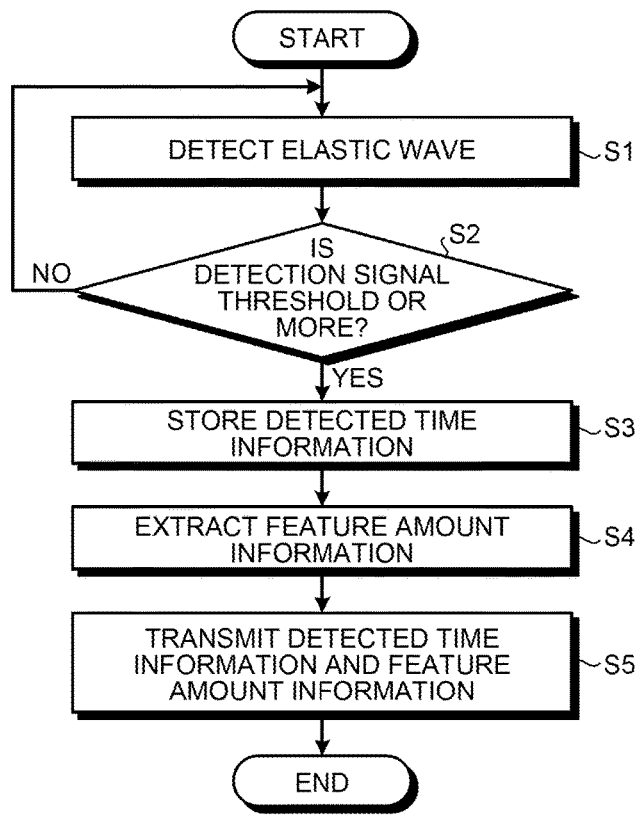
FIG. 11 is a diagram illustrating an example of display information indicating the number of ruptures of an embodiment.
FIG. 12 is a flowchart illustrating an example of a method of operating an end portion sensor unit of an embodiment.

FIG. 11 is a diagram illustrating an example of display information that indicates the number of ruptures of an embodiment. The example of FIG. 11 illustrates a case of displaying the total number of ruptures, the maximum number of ruptures per one pitch, and the maximum number of ruptures per one strand pitch, for each main rope 5. The total number of ruptures indicates the total number of the places where the wire cut has occurred. The maximum number of ruptures per one pitch indicates the number of ruptures of a place where the number of ruptures per one pitch is maximum. Note that the one pitch indicates a length of one strand going around the rope in a spiral manner. The maximum number of ruptures per one strand pitch indicates the number of ruptures of a place where the number of rupture per one strand pitch is maximum. Note that the one strand pitch indicates a length of a wire going around the strand in a spiral manner.

The display controller 57 performs display control of explicitly indicating that the deterioration is in progress by changing the color, the hatch pattern or the like of the total number of ruptures and display, when the total number of ruptures is a threshold (fifth threshold) or more. Further, the display controller 57 performs display control of explicitly displaying that the deterioration is in progress by changing the color, the hatch pattern or the like of the maximum number of ruptures per one pitch, when the maximum number of ruptures per one pitch is a threshold (sixth threshold) or more. Further, the display controller 57 performs display control of explicitly displaying that the deterioration is in progress by changing the color, the hatch pattern or the like of the maximum number of ruptures per one strand pitch, when the maximum number of ruptures per one strand pitch is a threshold (seventh threshold) or more.

In the example of FIG. 11, the total number of ruptures of the main rope 5c becomes the threshold or more, and thus the total number of ruptures of the main rope 5c is applied a hatch pattern by the display controller 57 and is displayed. Further, the maximum number of ruptures per one pitch of the main rope 5a is the threshold or more, and thus the maximum number of ruptures per one pitch of the main rope 5a is applied a hatch pattern by the display controller 57 and is displayed. Further, the maximum number of ruptures per one strand pitch of the main rope 5b is the threshold or more, the maximum number of ruptures per one strand pitch of the main rope 5b is applied a hatch pattern by the display controller 57 and is displayed.

Next, an example of a detection method of an embodiment will be described.

FIG. 12 is a flowchart illustrating an example of a method of operating the end portion sensor unit 20 of an embodiment. First, the AE sensor 21 detects the elastic wave generated from the main rope 5, and converts the elastic wave into the detection signal such as a voltage signal (step S1). Next, the extractor 25 determines whether the detection signal is the threshold or more (step S2). When the detection signal is less than the threshold (No in step S2), the processing is returned to step S1.

When the detection signal is the threshold or more (Yes in step S2), the extractor 25 stores the detected time information that indicates the time when the detection signal has been received (step S3). Next, the extractor 25 extracts the feature amount information that indicates the feature of the detection signal from the detection signal (step S4). Next, the communication unit 26 transmits the detected time information stored in the step S3 and the feature amount information extracted in step S4 to the server device 50 together with the identification information that indicates the AE sensor 21 that has detected the elastic wave as the end portion sensor unit detection information (step S5).

Figure 13:
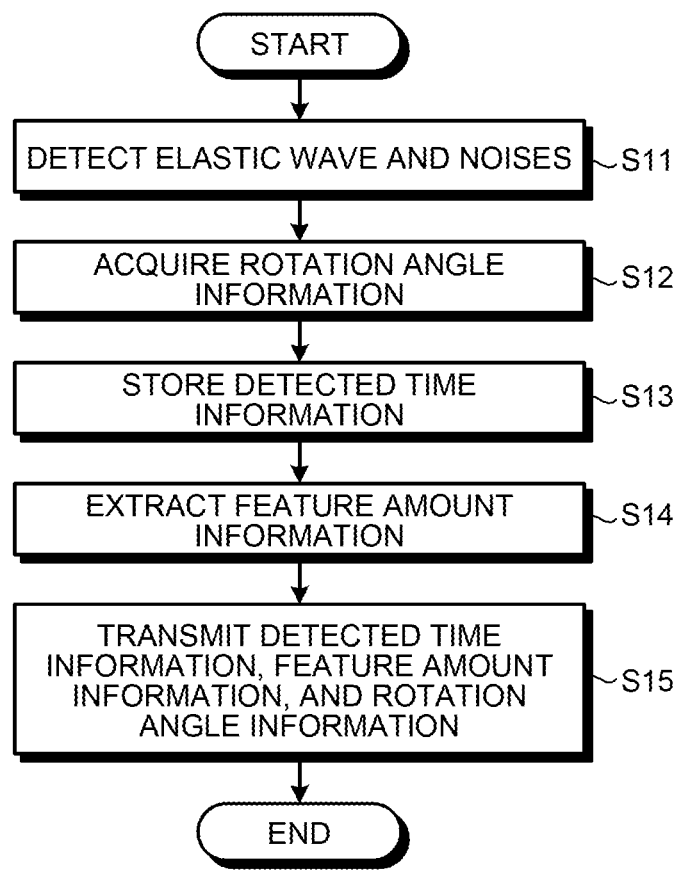
FIG. 13 is a flowchart illustrating an example of a method of operating a sheave sensor unit of an embodiment.

FIG. 13 is a flowchart illustrating an example of a method of operating the sheave sensor unit 30 of an embodiment. First, each of the AE sensors 31a to 31d detects the elastic wave and noises, and converts the elastic wave or the noises into the detection signal such as a voltage signal (step S11). Next, the acceleration sensor 37 detects the rotation angle φ (see FIG. 5) that indicates the position of the acceleration sensor 37 (step S12). Note that the processing of steps S1 and S2 is performed at the same timing.

Next, the extractor 35 stores the detected time information of the elastic wave and the noises detected in step S11 (step S13). Next, the extractor 35 extracts the feature amount information that indicates the feature of the detection signal from the detection signal (step S14). Next, the communication unit 36 transmits the detected time information stored in the step S13, the feature amount information extracted in step S14, and the rotation angle information acquired in step S12 in association with each other to the server device 50 as the sheave sensor unit detection information (step S15).

Figure 14:
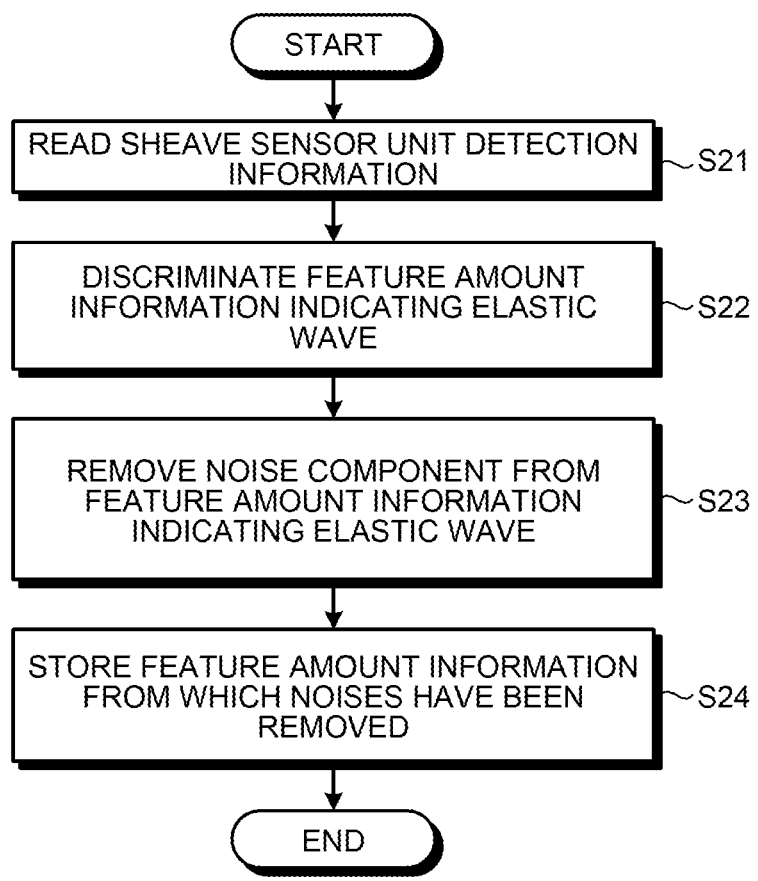
FIG. 14 is a flowchart illustrating an example of noise removal processing of a server device of an embodiment.

FIG. 14 is a flowchart illustrating an example of noise removal processing of the server device 50 of an embodiment. First, the discrimination unit 53 reads the sheave sensor unit detection information (the detected time information, the feature amount information, and the rotation angle information) from the storage 51 (step S21).

Next, the discrimination unit 53 discriminates the feature amount that indicates the elastic wave and the feature amount that indicates the noises from the rotation angle φ (see FIG. 5) that indicated by the rotation angle information by the above-described discrimination processing (step S22).

Next, the acquisition unit 54 acquires the feature amount information that indicates the elastic wave, from which the noises have been removed, by subtracting the feature amount information that indicates the noises from the feature amount information that indicates the elastic wave (step S23). Next, the acquisition unit 54 stores, in the storage 51, the feature amount information from which the noises have been removed in association with the sheave sensor unit detection information (step S24).

Figure 15:
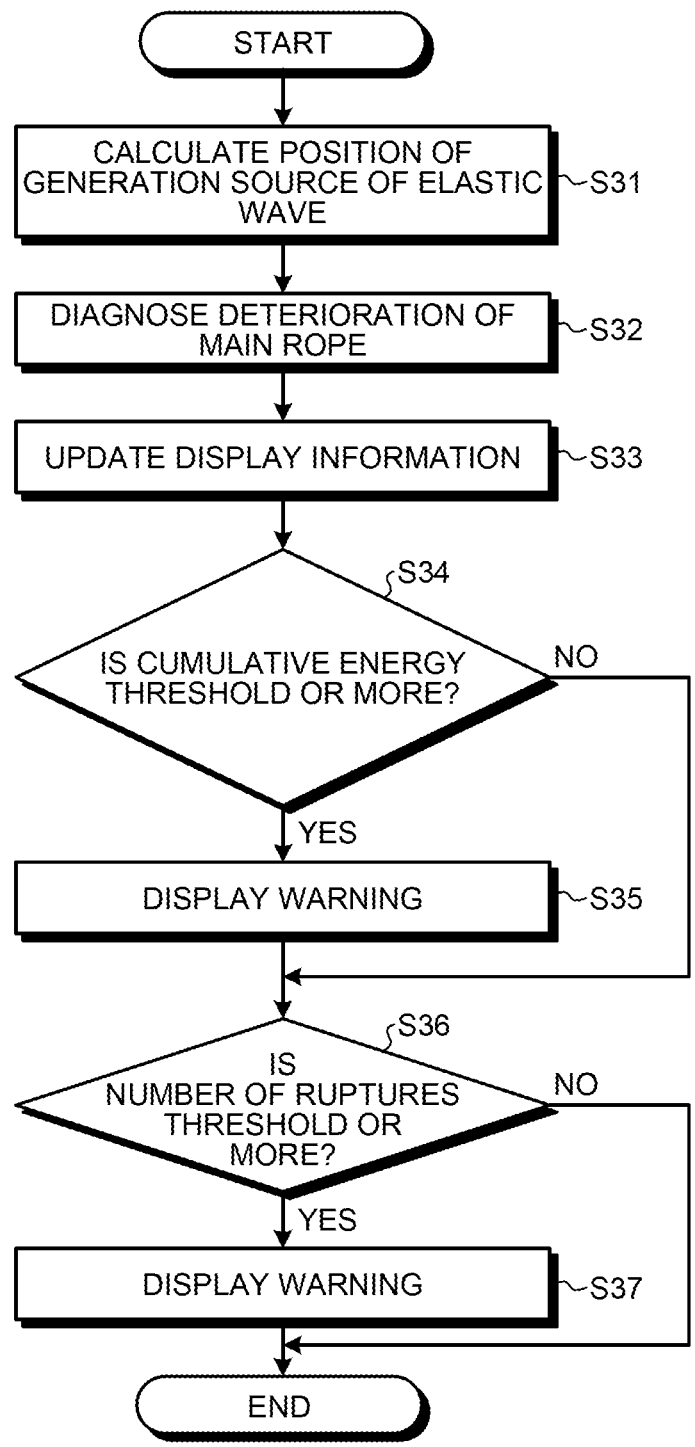
FIG. 15 is a flowchart illustrating an example of display processing of a server device of an embodiment.

FIG. 15 is a flowchart illustrating an example of display processing of the server device 50 of an embodiment. First, the calculator 55 reads the feature amount information of the end portion sensor unit detection information and the feature amount information of the sheave sensor unit detection information (from which the noises have been removed) from the storage 51, and calculates, by the above-described position calculation processing, the position of the main rope 8 where the elastic wave has been generated (step S31). The calculator 55 stores, in the storage 51, the deterioration positional information in which the positional information that indicates the generation source of the elastic wave and the feature amount information of the elastic wave are associated with each other.

Next, the diagnosis unit 56 diagnoses the deterioration of the main rope 5 based on the deterioration positional information (step S32). To be specific, the diagnosis unit 56 diagnoses the deterioration of the main rope 5 by determining whether there is the generation source where the cumulative energy of the elastic wave becomes the predetermined threshold or more.

Next, the display controller 57 updates the display information to be displayed in the display device based on the deterioration positional information and a diagnosis result obtained by the processing of step S32 (step S33). The display information is information as illustrated in FIGS. 9, 10, and 11, for example.

Next, when there is a place where the cumulative energy is the threshold (fourth threshold) or more (Yes in step S34), the display controller 57 displays, in the display device, the warning that indicates that the degree of deterioration of the main rope 5 is large in the place (step S35). When the cumulative energy is less than the threshold (No in step S35), the processing proceeds to step S36.

Next, the diagnosis unit 56 determines whether the number of ruptures of the wire of the main rope 5 is the threshold or more (step S36). To be specific, the diagnosis unit 56 determines whether there is the main rope 5 having the total number of ruptures being the threshold (fifth threshold) or more. Further, the diagnosis unit 56 determines whether there is the main rope 5 having the maximum number of ruptures per one pitch being the threshold (sixth threshold) or more. Further, the diagnosis unit 56 determines whether there is the main rope 5 having the maximum number of ruptures per one strand pitch being the threshold (seventh threshold) or more.

When the number of ruptures of the wire of the main rope 5 is the threshold or more (Yes in step S36), the display controller 57 displays the warning in the display device. For example, when the maximum number of ruptures per one pitch of the main rope 5a is the threshold (sixth threshold) or more, the display controller 57 displays, in the display device, the warning including the maximum number of ruptures per one pitch of the main rope 5a, and a message that indicates that the deterioration is in progress (step S37).

When the number of ruptures of the wire of the main rope 5 is less than the threshold (No in step S36), the processing is terminated.

As described above, in the detection system 100 of an embodiment, the calculator 55 calculates the position of the main rope 5 where the elastic wave has been generated, based on the propagating speed of the elastic wave, the time difference information of the detected times of the elastic waves detected by the AE sensor 21 installed at or near the end portion 6 (11) and the AE sensor 31 installed at the sheave 7 (8, 9, or 10), and the positions of the AE sensor 21 and the AE sensor 31. Accordingly, the detection system 100 can examine the state of the ropes without depending on the types of the ropes, in the state where the elevator is being operated.

Modification of Embodiment

Next, a modification of an embodiment will be described. In the modification of an embodiment, how to connect a sheave 8 and a hoist 12 is different from that in the embodiment (see FIG. 6).

Figure 16:
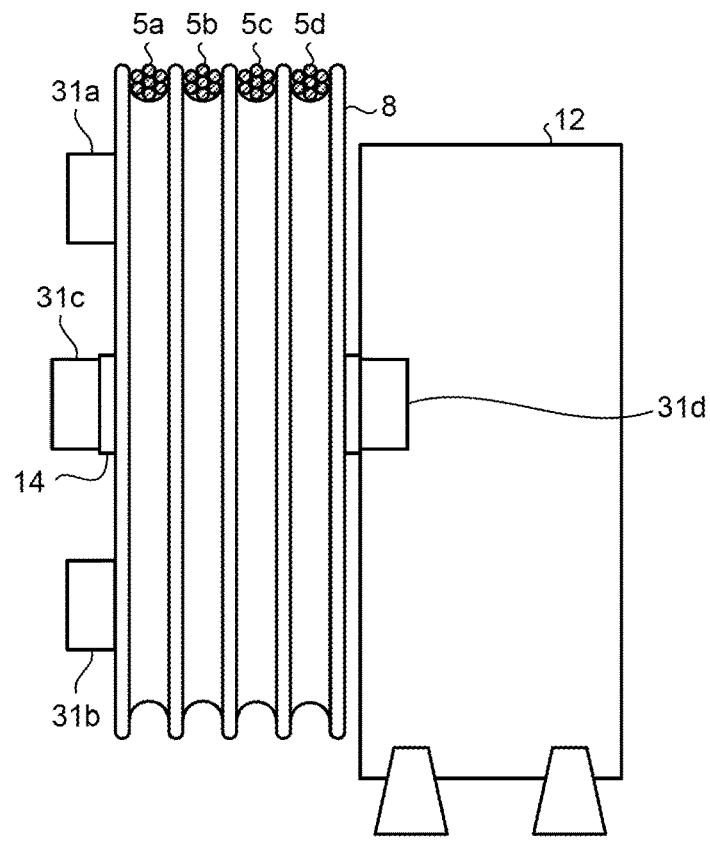
FIG. 16 is a diagram illustrating an example of an installation position of an AE sensor of a modification of an embodiment.

FIG. 16 is a diagram illustrating an example of installation positions of AE sensors 31 of the modification of an embodiment. The example of FIG. 16 illustrates a case in which the sheave 8 is directly connected with the hoist 12, and there is no bearing 15 (see FIG. 6) (so-called a cantilever structure). In this case, an AE sensor 31c is attached to a rotating shaft 14 outside the sheave 8. Further, an AE sensor 31d is attached to the rotating shaft 14 at an inner side of the hoist 12. Accordingly, the AE sensor 31c and the AE sensor 31d can be attached in a manner of sandwiching the sheave 8 form both sides. Note that description of attaching positions of the AE sensor 31a and the AE sensor 31b are the same as the case of FIG. 5, and is thus omitted.

By attaching the AE sensors 31c and 31d as described in FIG. 16, the elastic waves of the main ropes 5a to 5d can be detected from the both sides of the sheave 8. Therefore, a calculator 55 can calculate from which main rope 5 of the main ropes 5a to 5d the elastic wave has been generated.

Finally, an example of a hardware configuration of a server device 50 of an embodiment and a modification will be described.

Figure 17:
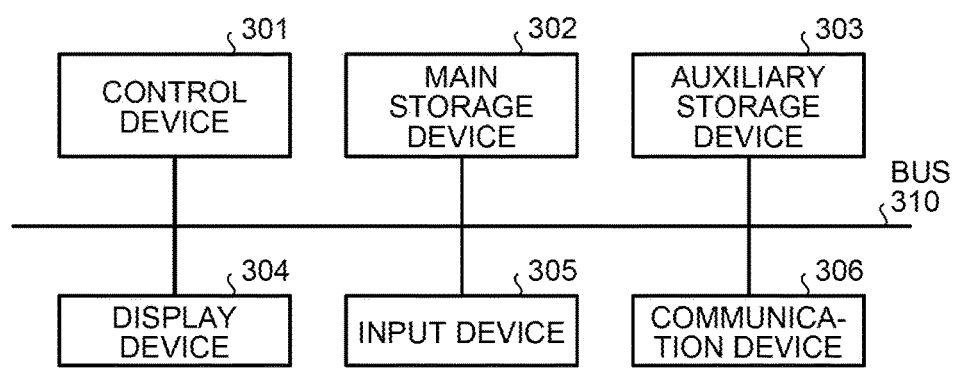
FIG. 17 is a diagram illustrating an example of a hardware configuration of a server device of an embodiment and a modification.

FIG. 17 is a diagram illustrating an example of a hardware configuration of the server device 50 of an embodiment and a modification. The server device 50 of an embodiment includes a control device 301, a main storage device 302, an auxiliary storage device 303, a display device 304, an input device 305, and a communication device 306. The control device 301, the main storage device 302, the auxiliary storage device 303, the display device 304, the input device 305, and the communication device 306 are connected through a bus 310. The server device 50 is a personal computer, a smart device, and the like, for example.

The control device 301 executes a program read to the main storage device 302 from the auxiliary storage device 303. The main storage device 302 is memories such as a read only memory (ROM) and a random access memory (RAM). The auxiliary storage device 303 is a hard disk drive (HDD), a memory card, and the like. The storage 51 of FIG. 7 corresponds to the main storage device 302 and the auxiliary storage device 303.

The display device 304 displays a state of the server device 50 and the like. The display device 304 is, for example, a liquid crystal display. The input device 305 is an interface for operating the server device 50. The input device 305 is a keyboard, a mouse, and the like, for example. When the server device 50 is smart devices such as a smart phone and a tablet terminal, the display device 304 and the input device 305 are a touch panel, for example. The communication device 306 is an interface for being connected to a network.

The program executed in the server device 50 of an embodiment is recorded in storage media readable by a computer, such as a CD-ROM, a memory card, a CD-R, and a digital versatile disk (DVD) in an installable format file or an executable format file, and is provided as a computer program product.

Further, the program executed in the server device 50 of an embodiment may be stored on a computer connected to a network 90 such as the Internet, and provided by being downloaded through the network 90. Further, the program executed in the server device 50 of an embodiment may be provided through the network 90 such as the Internet without being downloaded.

Further, the program of the server device 50 of an embodiment may be provided by being incorporated in a ROM or the like in advance.

The program executed in the server device 50 of an embodiment has a module configuration including the above-described function blocks (the communication unit 52, the discrimination unit 53, the acquisition unit 54, the calculator 55, the diagnosis unit 56, and the display controller 57) of FIG. 7. As actual hardware, the function blocks are loaded on the main storage device 302 by reading the program from the storage media and executing the program by the control device 301. That is, the function blocks are generated on the main storage device 302. Note that a part or all of the function blocks of FIG. 7 may be realized by hardware such as an integrated circuit (IC) or the like without being realized by software.

For example, the above-described detection system 100 of an embodiment may be applied to detection of deterioration of a wire rope used in cranes and bridges.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detection system that detects deterioration of a rope through at least one sheave, the system comprising:

a plurality of sensors configured to detect an elastic wave generated from the rope and convert the elastic wave into a detection signal, at least two of the sensors being installed at the sheave;

an extractor configured to extract feature amount information indicating a feature of the detection signal from the detection signal;

a discrimination unit configured to discriminate a first sensor that detects the elastic wave including a noise and a second sensor that detects the noise, based on a rotation angle of the sheave;

an acquisition unit configured to acquire the feature amount information indicating a feature of the detection signal indicating the elastic wave from which the noise has been removed, by subtracting the feature amount information indicating a feature of the detection signal acquired by the second sensor from the feature amount information indicating a feature of the detection signal acquired by the first sensor; and a calculator configured to recognize elastic waves detected by the respective sensors by using the feature amount information indicating a feature of the detection signal indicating the elastic wave from which the noise has been removed, calculate a position of the rope where the elastic wave has been generated, based on a propagating speed of the elastic wave, time difference information of a plurality of detected times of the elastic waves detected by the respective sensors, and positional information indicating positions of the respective sensors.

2. The system according to claim 1,
wherein the feature amount information includes at least one of an amplitude of a waveform of the detection signal, a duration of the waveform of the detection signal, the number of zero cross counts of the detection signal, energy of the waveform of the detection signal, and a frequency of the detection signal.

3. The system according to claim 1,
wherein the sensors installed at the sheave are two as a set, and
the discrimination unit discriminates the sensor closer to the rope as the first sensor, and discriminates the sensor farther from the rope as the second sensor, based on the rotation angle of the sheave.

4. The system according to claim 3,
wherein the set of two sensors is arranged such that a phase difference between the rotation angle of the sheave in a position where the one sensor is installed and the rotation angle of the sheave in a position where the other sensor is installed becomes $\pi$.

5. The system according to claim 1,
wherein the rope includes a plurality of main ropes used in an elevator, and the two or more sensors installed at the sheave are installed on both surfaces of the sheave, and calculate a main rope where the elastic wave has been generated based on a difference in the feature amounts indicating features of the detection signals acquired at the both surfaces of the sheave.

6. The system according to claim 5, further comprising:
a detector configured to detect a position of a car of the elevator and acquire car positional information indicating the position of the car according to a time,
wherein the positional information includes distance information indicating a distance between the sheave and an end portion of the rope and a distance between the sheaves, the positional information being determined according to the position of the car indicated by the car positional information at a detected time of the sensor that has first detected the elastic wave.

7. A detection method for a detection system that detects deterioration of a rope through at least one sheave by a plurality of sensors, at least two of the sensors being installed at the sheave, the method comprising:

detecting, by the sensors, an elastic wave generated from the rope;

converting, by the sensors, the elastic wave into a detection signal;

extracting, by an extractor, feature amount information indicating a feature of the detection signal from the detection signal;

discriminating, by a discrimination unit, a first sensor that detects the elastic wave including a noise and a second sensor that detects the noise, based on a rotation angle of the sheave;

acquiring, by an acquisition unit, the feature amount information indicating a feature of the detection signal indicating the elastic wave from which the noise has been removed, by subtracting the feature amount information indicating a feature of the detection signal acquired by the second sensor from the feature amount information indicating a feature of the detection signal acquired by the first sensor;

recognizing, by a calculator elastic waves detected by the respective sensors by using the feature amount information indicating a feature of the detection signal indicating the elastic wave from which the noise has been removed; and calculating, by the calculator, a position of the rope where the elastic wave has been generated based on a propagating speed of the elastic wave, time difference information of a plurality of detected times of the elastic waves detected by the respective sensors, and positional information indicating positions of the respective sensors.

* * * * *